United States Patent [19]
Bucholz

[11] Patent Number: 5,383,454
[45] Date of Patent: Jan. 24, 1995

[54] SYSTEM FOR INDICATING THE POSITION OF A SURGICAL PROBE WITHIN A HEAD ON AN IMAGE OF THE HEAD

[75] Inventor: Richard D. Bucholz, St. Louis, Mo.

[73] Assignee: St. Louis University, St. Louis, Mo.

[21] Appl. No.: 909,097

[22] Filed: Jul. 2, 1992

Related U.S. Application Data

[63] Continuation of Ser. No. 600,753, Oct. 19, 1990, abandoned.

[51] Int. Cl.$^6$ .............................................. A61B 5/103
[52] U.S. Cl. ..................................... 128/653.1; 606/130
[58] Field of Search ................... 606/130; 128/653.01, 128/653.02, 653.05; 364/413.01, 413.22; 340/870.11, 853.1, 853.2

[56] References Cited

U.S. PATENT DOCUMENTS

| | | | |
|---|---|---|---|
| 3,821,469 | 6/1974 | Whetstone et al. | 178/18 |
| 3,983,474 | 9/1976 | Kuipers | 324/43 R |
| 4,182,312 | 1/1980 | Mushabac | 433/68 |
| 4,341,220 | 7/1982 | Perry | 128/630 |
| 4,608,977 | 9/1986 | Brown | 128/303 B |
| 4,638,798 | 1/1987 | Sheldon et al. | 128/303 B |
| 4,651,732 | 3/1987 | Frederick . | |
| 4,660,970 | 4/1987 | Ferrano | 356/1 |
| 4,701,049 | 10/1987 | Beckmann et al. | 356/1 |
| 4,705,395 | 11/1987 | Hagenier et al. | 356/1 |
| 4,705,401 | 11/1987 | Addleman et al. | 356/376 |
| 4,706,665 | 11/1987 | Gouda . | |
| 4,709,156 | 11/1987 | Murphy et al. | 250/560 |
| 4,723,544 | 2/1988 | Moore et al. . | |
| 4,733,969 | 3/1988 | Case et al. | 356/375 |
| 4,737,032 | 4/1988 | Addleman et al. | 356/376 |
| 4,743,770 | 5/1988 | Lee | 250/560 |
| 4,743,771 | 5/1988 | Sacks et al. | 250/560 |
| 4,745,290 | 5/1988 | Frankel et al. | 250/560 |
| 4,750,487 | 6/1988 | Zanetti . | |
| 4,753,528 | 6/1988 | Hines et al. | 356/1 |
| 4,761,072 | 8/1988 | Pryor | 356/1 |
| 4,764,016 | 8/1988 | Johanasson | 356/371 |
| 4,779,212 | 10/1988 | Levy | 364/562 |
| 4,782,239 | 11/1988 | Hirose et al. | 250/561 |
| 4,791,934 | 12/1988 | Brunnett | 128/653 |
| 4,794,262 | 12/1988 | Sato et al. | 250/560 |
| 4,805,615 | 2/1989 | Carol . | |
| 4,809,694 | 3/1989 | Ferrara . | |

(List continued on next page.)

FOREIGN PATENT DOCUMENTS

| | | | |
|---|---|---|---|
| 0062941 | 10/1982 | European Pat. Off. | A61B 5/10 |
| 3508730 | 9/1986 | Germany | A61B 5/10 |
| 62-000327 | 1/1987 | Japan . | |
| 2094590 | 9/1982 | United Kingdom | 128/653.1 |
| WO88/09151 | 12/1988 | WIPO | A61B 19/00 |
| WO90/05494 | 5/1990 | WIPO . | |
| WO91/07726 | 5/1991 | WIPO . | |

OTHER PUBLICATIONS

Watanabe et al, "Three Dimensional Digitizer (Neuronavigator): New Equipment for Computed Tomography-Guided Stereotaxic Surgery", 27 Surg. Neurol, 543-7 (1987).

(List continued on next page.)

Primary Examiner—Lee S. Cohen
Assistant Examiner—Samuel Gilbert
Attorney, Agent, or Firm—Senniger, Powers, Leavitt & Roedel

[57] ABSTRACT

A system for indicating a position of a tip of a probe which is positioned within an object on cross-sectional, scanned images of the object. The object includes reference points and the images of the object include reference images corresponding to the reference points. An array for receiving radiation emitted from the probe and from time reference points is digitized by a three dimensional digitizer to measure the position of the tip of the probe relative to the reference points of the object:. A computer employing translational software translates the position of the tip of the probe into a coordinate system corresponding to the coordinate system of the cross-sectional images. A stereotactic imaging system selects the image of the object closest to the measured position of the tip of the probe and displays the selected image and a cursor representing the position of the tip of the probe on the selected images.

20 Claims, 7 Drawing Sheets

U.S. PATENT DOCUMENTS

| | | | |
|---|---|---|---|
| 4,821,200 | 4/1989 | Oberg | 364/474.24 |
| 4,822,163 | 4/1989 | Schmidt | 356/1 |
| 4,825,091 | 4/1989 | Breyer et al. | 250/560 |
| 4,829,373 | 5/1989 | Leberl et al. | 358/88 |
| 4,836,778 | 6/1989 | Baumrind et al. | 433/69 |
| 4,841,967 | 6/1989 | Chang et al. | |
| 4,875,478 | 10/1989 | Chen | |
| 4,931,056 | 6/1990 | Ghajar et al. | 606/130 |
| 4,945,914 | 8/1990 | Allen | 128/653 R |
| 4,991,579 | 2/1991 | Allen | 128/653 R |
| 5,016,639 | 5/1991 | Allen | 128/653 R |
| 5,017,139 | 5/1991 | Mushabac | 433/109 |
| 5,027,818 | 7/1991 | Bova et al. | 128/653.1 |
| 5,094,241 | 3/1992 | Allen | 128/653.1 |
| 5,097,839 | 3/1992 | Allen | 128/653.1 |
| 5,099,846 | 3/1992 | Hardy | 606/130 X |
| 5,107,839 | 4/1992 | Houdek et al. | 606/130 X |
| 5,119,817 | 6/1992 | Allen | 128/653.1 |
| 5,142,930 | 9/1992 | Allen et al. | 74/469 |
| 5,178,164 | 1/1993 | Allen | 128/898 |
| 5,197,476 | 3/1993 | Nowacki et al. | 128/660.03 |
| 5,211,164 | 5/1993 | Allen | 128/653.1 |
| 5,224,049 | 6/1993 | Mushabac | 364/474.05 |

OTHER PUBLICATIONS

Reinhardt et al, "A Computer Assisted Device for the Intra Operative CT-Correlated Localization of Brain Tumors", Eur. Surg. Res. 20:52–58 (1988).

Friets et al., "A Frameless Stereotaxic Operating Microscope for Neurosurgery", IEEE Transactions on Biomedical Engineering 36, No. 6 (Jun. 1989), pp. 608, 613–617.

Roberts et al., "A Frameless Sterotaxic Integration of Computerized Tomographic Imaging and the Operating Microscope" J. Neurosurg 65: 545–549 (1986), pp. 545–549.

"SACDAC User's Guide, Version 2e" (Mar. 1989) by PixSys, Inc., pp. 0–1 Thru 5–3.

"Offset Probe for Science Accessories' Gp-8-3d digitizer" (Dec. 1987) by PixSys, Inc., one page.

"Alignment Procedure for the PixSys Two-Emitter Offset Probe for the SAC GP-8-3d Sonic Digitizer" (undated) by PixSys, Inc., 3 unnumbered pages.

"PixSys: 3-D Digitizing Accessories" (Aug. 1989) by PixSys, Inc., 6 unnumbered pages.

"Design Aide" (Mar. 1989) by PixSys, Inc., 5 unnumbered pages.

"3-D Digitizer Captures the World" (Oct. 1990) BYTE Magazine, p. 43.

An Articulated Neurosurgical Navigation System Using MRI and CT Images (Feb., 1988) by Yukio Kosugi et al.

A New Imaging Method for Intraoperative Therapy Control in Skull-Base Surgery (1988) by Ralph Mosges et al.

A Frameless Stereotaxic Integration of Computerized Tomographic Imaging and the Operating Microscope (Oct., 1986) by David W. Roberts, M.D. et al.

Computed Tomography-Guided Stereotactic Systems (1983) by M. Peter Heilbrun, M.D.

Computed Tomography-Directed Stereotaxy for Biopsy and Interstitial Irradiation of Brain Tumors: Technical Note (1982) by Alexander R. MacKay, M.D. et al.

Computed Tomographic Guidance Stereotaxis in the Management of Intracranial Mass Lesions (1983) by M. L. J. Apuzzo et al.

A Comparison of CT-Stereotaxic Brain Biopsy Techniques (Apr. 12, 1984) by Neil B. Horner, M.D. et al.

Computed Tomography Plane of the Target Approach in Computed Tomographic Stereotaxis (1984) by Arun-Angelo Patil, M.D.

Trigeminus Stereoguide: An Instrument for Stereotactic Approach Through the Foramen Ovale and Foramen Jugulare (1984) by Lauri V. Laitinen, M.D.

CT-Guided Stereotactic Biopsies Using a Modified Frame and Gildenberg Techniques (Jan. 5, 1984) by D. E. Bullard et al.

A Multipurpose CT-Guided Stereotactic Instrument of Simple Design (1983) by J. M. Van Buren et al.

Computer-Assisted Stereotaxic Laser Resection of Intra-Axial Brain Neoplasms (Mar., 1986) by Patrick J. Kelly, M.D. et al.

Three-Dimensional Digitizer (Neuronavigator): New Equipment for Computed Tomography-Guided Stereotaxic Surgery (1987) by Eiju Watanabe, M.D. et al.

FIG. IC
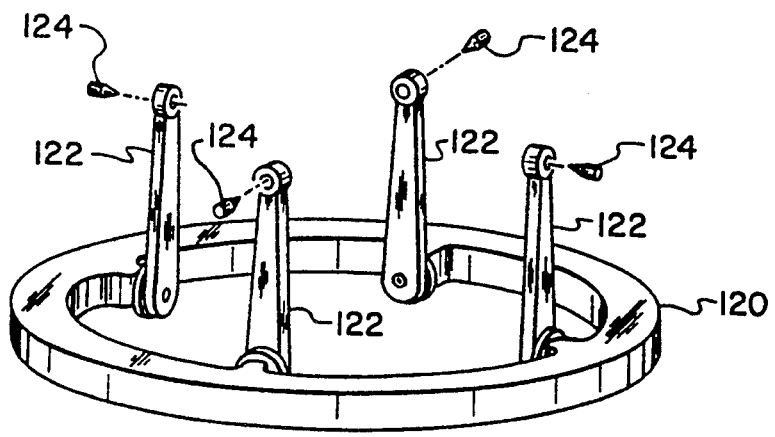
FIG. ID
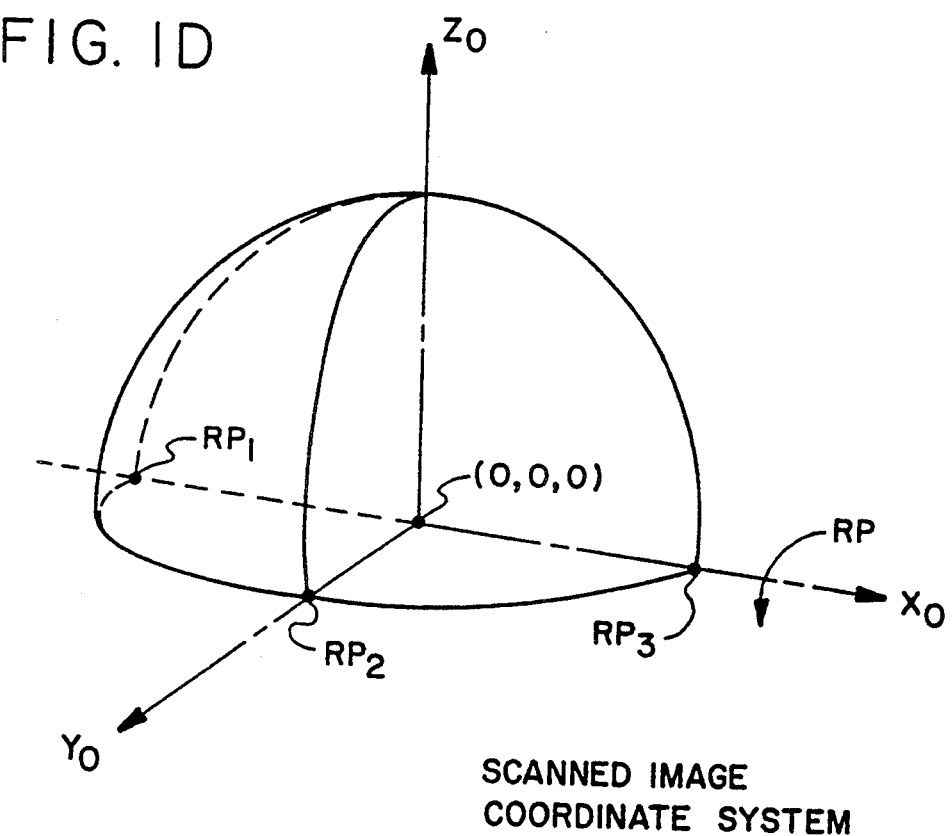
SCANNED IMAGE
COORDINATE SYSTEM

SURGICAL PROBE
COORDINATE SYSTEM

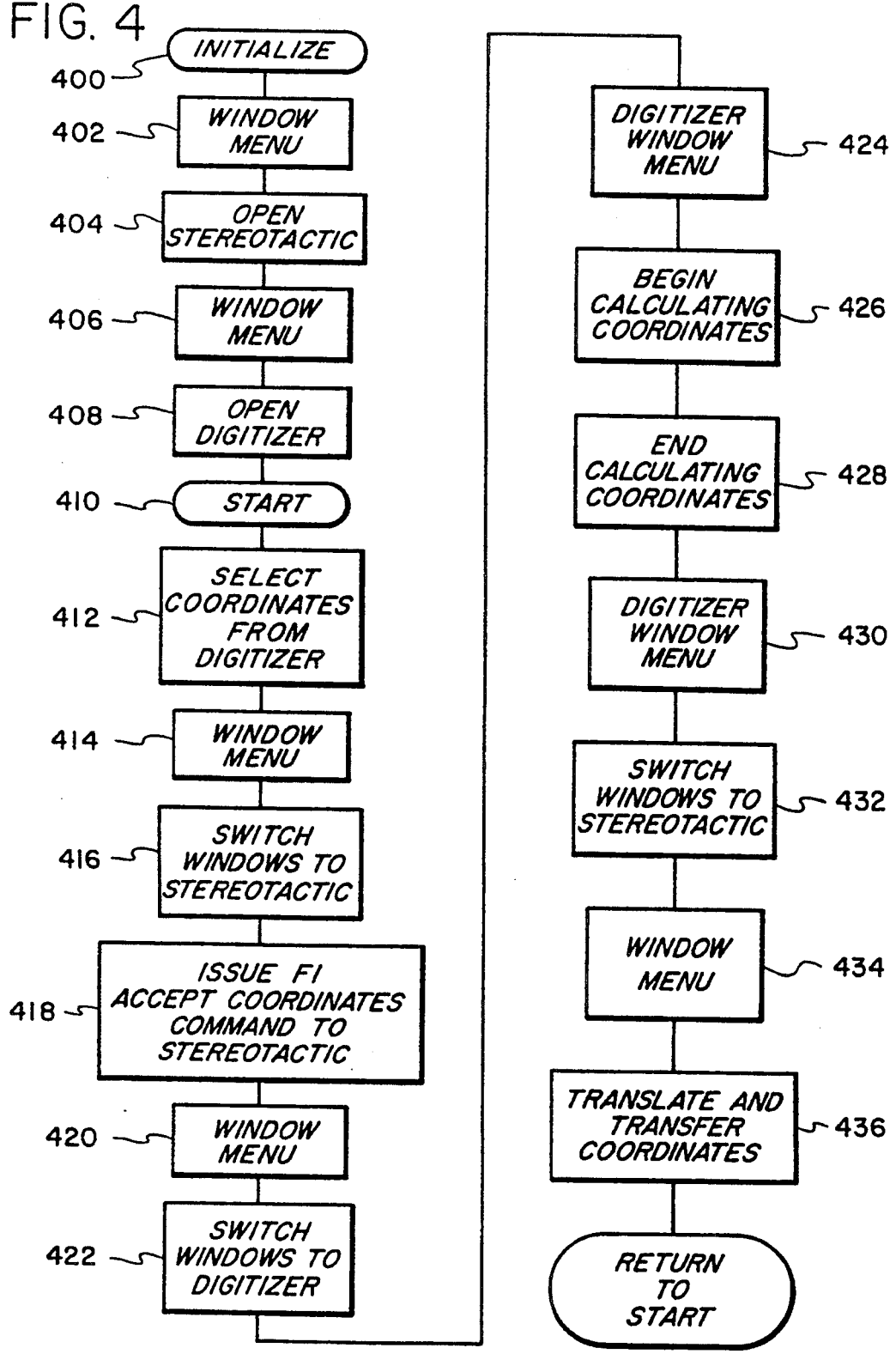

SYSTEM FOR INDICATING THE POSITION OF A SURGICAL PROBE WITHIN A HEAD ON AN IMAGE OF THE HEAD

This is a continuation of application Ser. No. 07/600 753, filed Oct. 19, 1990, now abandoned.

BACKGROUND OF THE INVENTION

Precise localization of position has always been critical to neurosurgery. Knowledge of the anatomy of the brain and specific functions relegated to local areas of the brain are critical in planning any neurosurgical procedure. Recent diagnostic advances such as computerized tomographic (CT) scans, magnetic resonance imaging (MRI) scanning, and positron emission tomographic (PET) scanning have greatly facilitated preoperative diagnosis and surgical planning. However, the precision and accuracy of the scanning technologies have not become fully available to the neurosurgeon in the operating room. Relating specific structures and locations within the brain during surgery to preoperative scanning technologies has previously been cumbersome, if not impossible.

Stereotactic surgery, first developed 100 years ago, consists of the use of a guiding device which channels the surgery through specific parts of the brain as localized by preoperative radiographic techniques. Stereotactic surgery was not widely used prior to the advent of modern scanning technologies as the injection of air into the brain was required to localize the ventricles, fluid containing chambers within the brain. Ventriculography carried a significant complication rate and accuracy in localization was marginal.

SUMMARY OF THE INVENTION

It is an object of this invention to provide a system which can determine the position of a probe within a head and display an image corresponding to the determined position.

The invention comprises a system for indicating a position of a tip of a probe which is positioned within an object on images of the object, wherein the object includes reference points and the images of the object include reference images corresponding to the reference points. The system comprises measuring means, translating means and selecting and displaying means. The measuring means measures the position of the tip of the probe relative to the reference points of the object. The translating means translates the position of the tip of the probe into a coordinate system corresponding to the images. The selecting and displaying means selects the image of the object which corresponds to the measured position of the tip of the probe and displays the selected image.

The invention also comprises a system for indicating a position of a tip of a surgical probe which is positioned within a head of a body of a patient on images of the head, wherein the head includes reference points and the images of the head include reference images corresponding to the reference points. Means measures the position of the tip of the surgical probe relative to the reference points of the head. Means translates the position of the tip of the surgical probe into a coordinate system corresponding to the images. Means selects the image of the head which corresponds to the measured position of the tip of the surgical probe and displays the selected image.

The invention also comprises a method for indicating a position of a tip of a surgical probe which is positioned within a head of a body of a patient on images of the head, wherein the head includes reference points and the images of the head include reference images corresponding to the reference points, said method comprising the steps of: measuring the position of the tip of the surgical probe relative to the reference points of the head; translating the position of the tip of the surgical probe into a coordinate system corresponding to the images; selecting the image of the head which corresponds to the measured position of the tip of the surgical probe; and displaying the selected image.

Other objects and features will be in part apparent and in part pointed out hereinafter.

BRIEF DESCRIPTION OF THE DRAWINGS

FIG. 1C is a perspective illustration of a reference ring which is mounted by uprights to a patient's head to support the cylindrical frame structure of FIG. 1A.

FIG. 1D is a perspective illustration of the coordinate system of a three dimensional scanned image.

FIG. 4 is a flow chart of the translational software for translating coordinates from the surgical probe coordinate system to the scanned image coordinate system according to the invention.

Corresponding reference characters indicate corresponding parts throughout the several views of the drawings.

DETAILED DESCRIPTION OF THE PREFERRED EMBODIMENTS

With the advent of modern scanning equipment and techniques, several stereotactic systems have been developed and are presently available. These stereotactic systems allow a surgeon to localize specific points detected on CT, MRI or PET scans which have been previously generated prior to the surgical procedure being performed. In particular, the stereotactic systems allow the selection of specific points detected on the scans to be localized within the brain by the surgeon during the surgical procedure using a mechanical device.

Figure 1A:
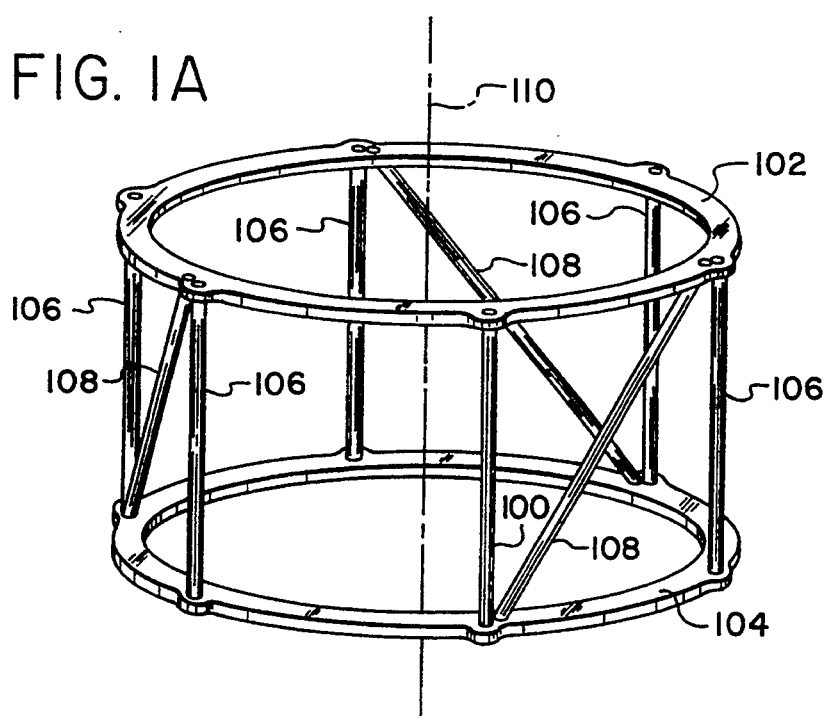
FIG. 1A is a perspective illustration of a cylindrical frame structure which is mounted around a patient's head during the scanning process.
Figure 1B:
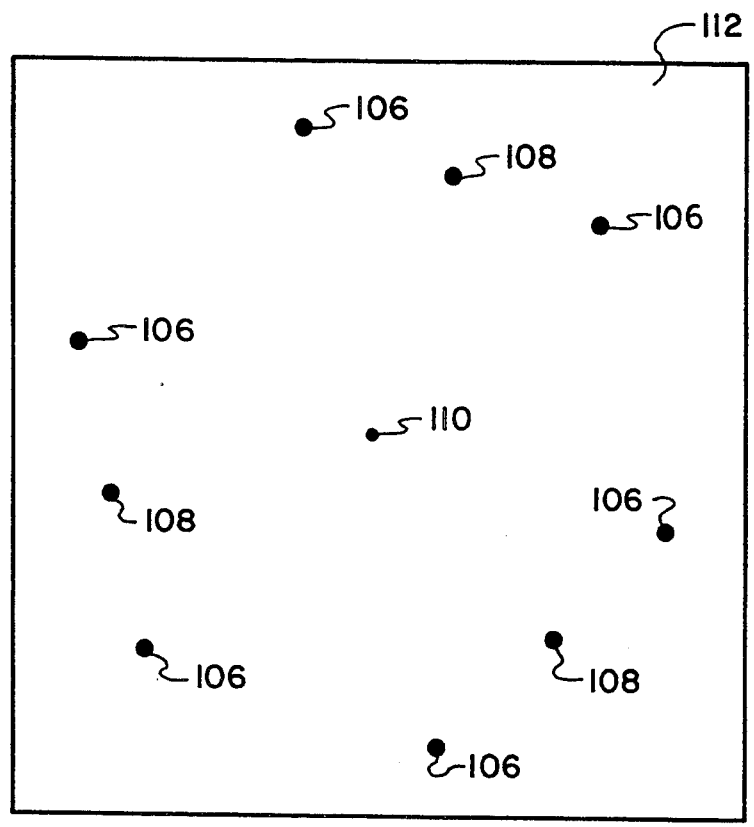
FIG. 1B is a plan view of the rods of the cylindrical frame structure of FIG. 1A taken along a plane midway between the upper and lower rings.

Initially, prior to the operative procedure, some form of localizing device, such as a frame, is attached to the patient's skull using sharp pins. The particular scan or scans which are to be performed are then generated with the head of the patient encircled by the frame. For example, the frame may be comprised of a cylindrical structure 100 as illustrated in perspective in FIG. 1A. Structure 100 includes an upper circular ring 102 and a lower circular ring 104 which are interconnected by six vertical rods 106 and three diagonal rods 108. The three diagonal rods 108 diagonally interconnect rings 102 and 104 so that any plane which passes through the cylindrical structure 100 and orthogonally intersects its axis 108 will intersect each of the diagonal rods 108 at a particular point. The resultant spacing between the diagonal and upright rods defines a unique plane within the cylindrical structure 100. For example, as shown in FIG. 1B, a scan in a particular plane would show a pattern of six cross-sectional views of the rods 106 108. The unique spacing of these views of the rods, as shown in plane 112 of FIG. 1B, would necessarily indicate that the position of the scan plane 112 was parallel to and midway between rings 102 and 104 of the cylindrical structure 100.

As a result of the scanning process, the images obtained are analyzed and the position within the images of the specific marking rods 106 108, called fudicels, are identified and measured. By measuring the distance between the rods 106 and 108, the specific location of a scan with reference to a base plane can be identified. Generally, the lower ring 104 of the cylindrical structure 100 is attached to a reference ring 120 (also known as a BRW head ring) as illustrated in FIG. 1C. As noted above, this ring 120 is supported on the patient's head via uprights 122 attached to the lead by the use of sharp pins 124 so that the ring 120 is held firmly in place with respect to the head. The lower ring 104 of the cylindrical structure 100 is mounted to the reference ring 120 attached to the patient's head so that these two rings are in parallel planes.

As shown in FIG. 1D, the scanning system (e.g., CT, MRI, PET) which is performing the scanning has a scanned image coordinate system $(X_0, Y_0, Z_0)$ within which a reference plane RP can be defined by at least three reference points RP1, RP2 and RP3 located on the head 124 of the patient. A computer is then used to calculate a specific position within the brain and a target picked out on the specific image can be approached with a fair degree of accuracy during the surgical procedure.

Although stereotactic surgery allows a surgeon to be guided to a specific point with accuracy, it has not been particularly useful in allowing the surgeon to identify the particular location of a surgical probe within the brain at any point during the surgical process. Frequently in neurosurgery, brain tumors or other target points within the brain are indistinguishable from surrounding normal tissue and may not be detected even with the use of frozen sections. Moreover, with modern microsurgical techniques, it is essential that the neurosurgeon identify specific structures within the brain which are of critical functional importance to the patient. In addition, the boundaries of these structures must be accurately defined and specifically known to the surgeon during the surgical process. In this way, these tissues will not be disturbed or otherwise damaged during the surgical process resulting in injury to the patient.

Figure 2A:
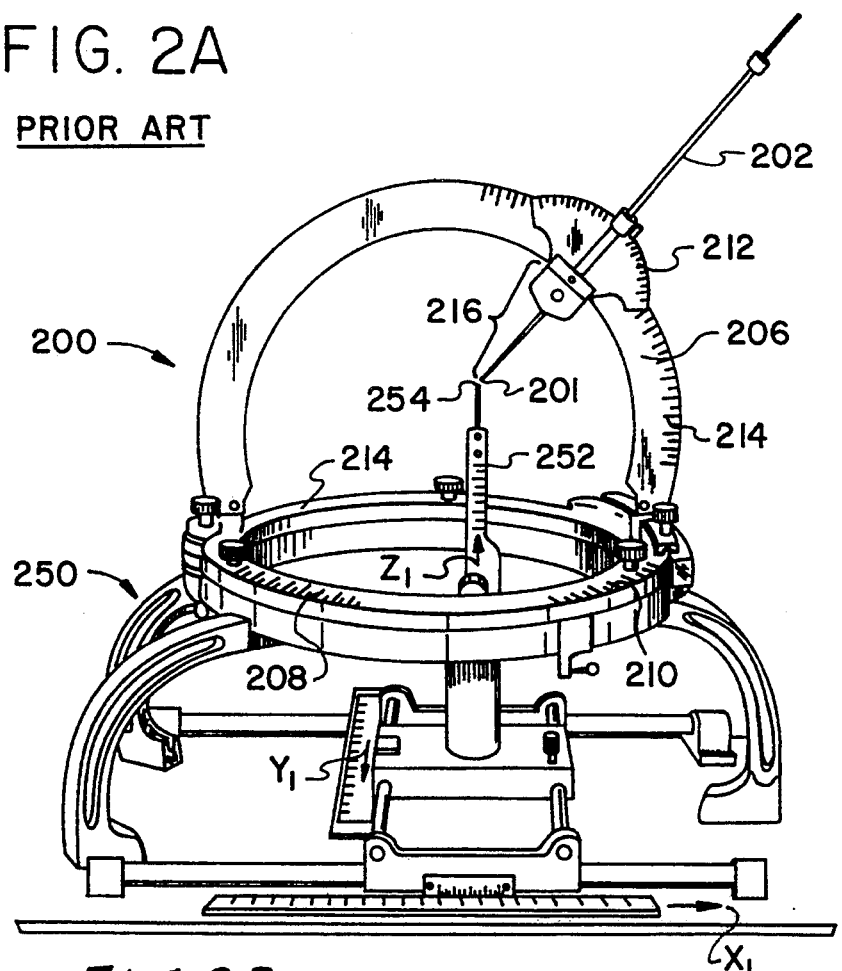
FIG. 2A is a perspective view of the caliper frame used in the prior art to determine the relative position between a position in the head and the phantom base.
Figure 2B:
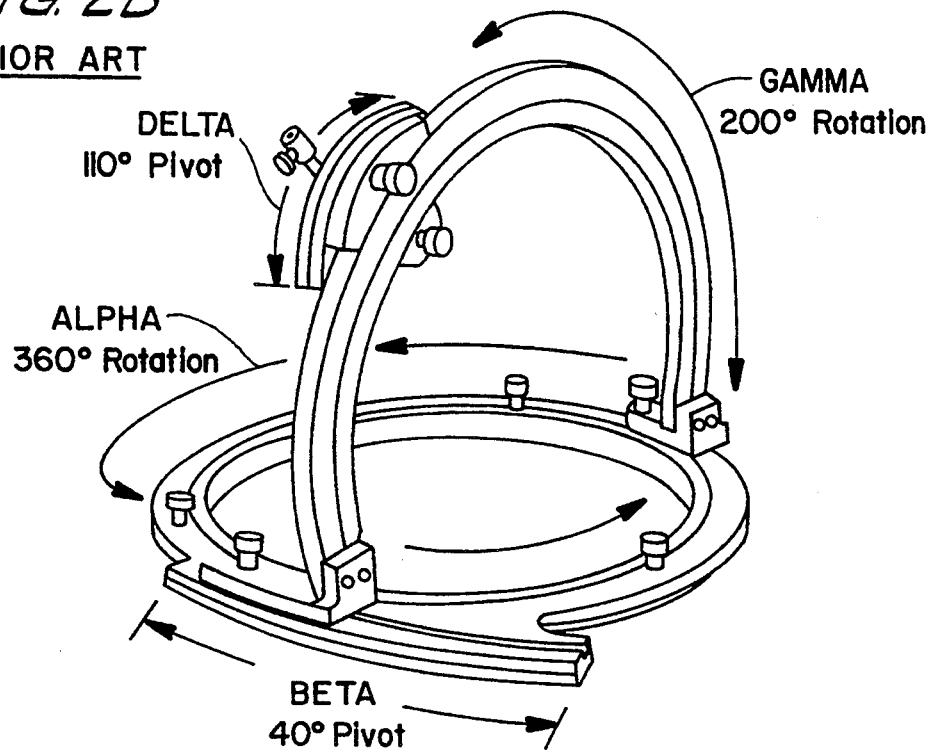
FIG. 2B is a perspective view prior art of the caliper frame of FIG. 2A illustrating its angles of adjustment.

In the past, the surgeon has been able to use the stereotactic system in reverse in order to permit the determination of the position of a surgical probe relative to the scanned images so the image corresponding to the probe position can be identified and viewed. However, going in reverse from the patient's brain backwards to find the position of the surgical probe relative to the scan is a cumbersome and time-consuming process. Usually, a specially designed caliper frame 200, as illustrated in FIG. 2A, has to be attached to the ring 120 affixed to the patient's head to determine the position of the surgical probe in the head. For example, suppose the surgeon desires to know the position of a tip 201 of a probe 202 in the patient's head. First, the caliper frame 200 is fitted to the reference ring 120 affixed to the patient's head. Next, the position of probe 202 is positioned on arch 206 and the frame 200 is set to indicate the alpha, beta, gamma and delta angles on scales 208, 210, 212 and 214 that the probe 202 defines with respect to the frame 200, as shown in FIG. 2B. Next, the distance 216 from the tip of the probe 202 to the arch 206 is determined.

The caliper frame 200 is then transferred and mounted to a phantom base 250 in a manner as illustrated in FIG. 2A. The phantom base 216 has a coordinate system $(X_1, Y_1, Z_1)$. Generally, the caliper frame 200 identifies a point 201 over the phantom base 250. A pointing device 252 is positioned to have its tip 254 at point 201. The $X_1-Y_1$ plane of the phantom base 200 corresponds to a plane parallel to the plane in which the reference points RP1, RP2 and RP3 are located. The $(X_1, Y_1, Z_1)$ coordinates define the position of point 201. As a result, the position of point 254 with respect to the $X_1-Y_1$ plane and, therefore, with respect to the reference plane RP is now known. A computer can now be used to calculate the specific position within the brain and the particular scan which corresponds to the calculated position can now be accessed and viewed on a scanning system.

Figure 2C:
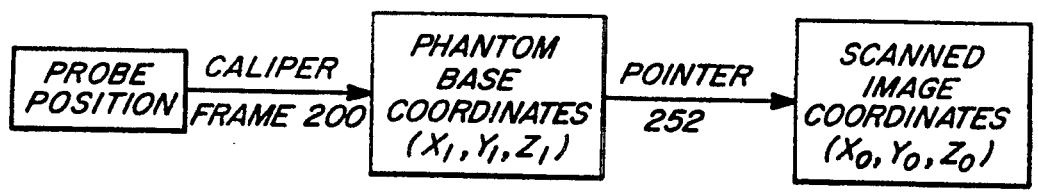
FIG. 2C is a block diagram of the steps involved in the prior art process of determining the position of surgical probe relative to the scanned images so that the image corresponding to the probe position can be identified and viewed by the surgeon.

In summary, this prior art process as shown in FIG. 2C identifies the location of the tip 201 of the surgical probe 202 for the surgeon. Initally, the surgeon positions the probe 202 on the caliper frame 200, which is attached to the head, at the position desired within the head. The caliper frame 200 is then removed from the patient's head and transferred to the phantom base 250. The pointing device 252 is then positioned at point 254 which is essentially coaxial with point 201 of the tip of the probe. The pointing device 252 then indicates the position of the tip of the probe in the phantom base coordinate system $(X_1, Y_1, Z_1)$. Finally, these coordinates are used to determine the scanned image coordinates $(X_0, Y_0, Z_0)$ so that the image corresponding to the probe position can be displayed.

After this cumbersome and time-consuming process, the surgeon has now determined the position of the tip 201 of the probe 202 with respect to the scanned images and can now view the image corresponding to the probe position to decide the next step in the surgical procedure. This entire process takes approximately ten to fifteen minutes and increases the risks of intraoperative contamination as the base of the calipers are non-sterile. Because of these considerations, stereotactic surgery is not commmonly employed in most procedures. Furthermore, the minimal accuracy it affords is generally insufficient for modern microsurgical techniques. Consequently, stereotactic surgery is not generally available to the majority of certain patients undergoing surgery.

Figure 2D:
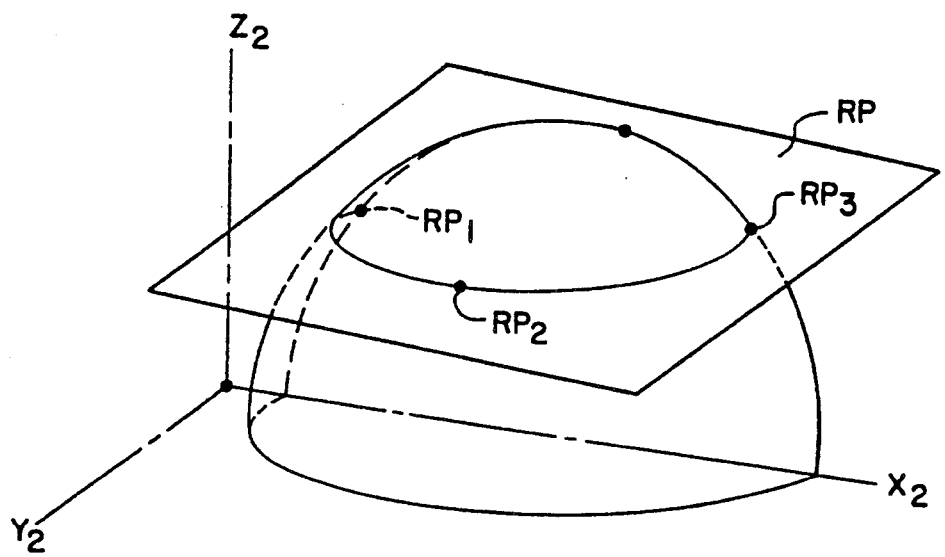
FIG. 2D is a perspective illustration of a three dimensional coordinate system of a surgical probe.

Comparing FIGS. 1D and 2A, it can be seen that it is necessary for the surgeon to know the specific location of the tip 201 of the surgical probe 202 with respect to the scanned image coordinate system ($X_0$, $Y_0$, $Z_0$) of the particular scans that were preoperatively performed. In other words, the surgical probe 202 has a particular coordinate system ($X_2$, $Y_2$, $Z_2$) which is illustrated in FIG. 2D. Ideally, the surgical probe coordinate system ($X_2$, $Y_2$, $Z_2$) must be related to the scanned image coordinate system ($X_0$, $Y_0$, $Z_0$). The prior art as illustrated in FIG. 2B has suggested relating these coordinate systems via the phantom base coordinate system ($X_1$, $Y_1$, $Z_1$). However, as noted above, this relational process is inaccurate, time-consuming and cumbersome. The invention uses a 3D digitizer system to locate the position of the tip 201 of the surgical probe 202 and to directly relate the surgical probe coordinate system ($X_2$, $Y_2$, $Z_2$) to the scanned image coordinate system ($X_0$, $Y_0$, $Z_0$).

Figure 3A:
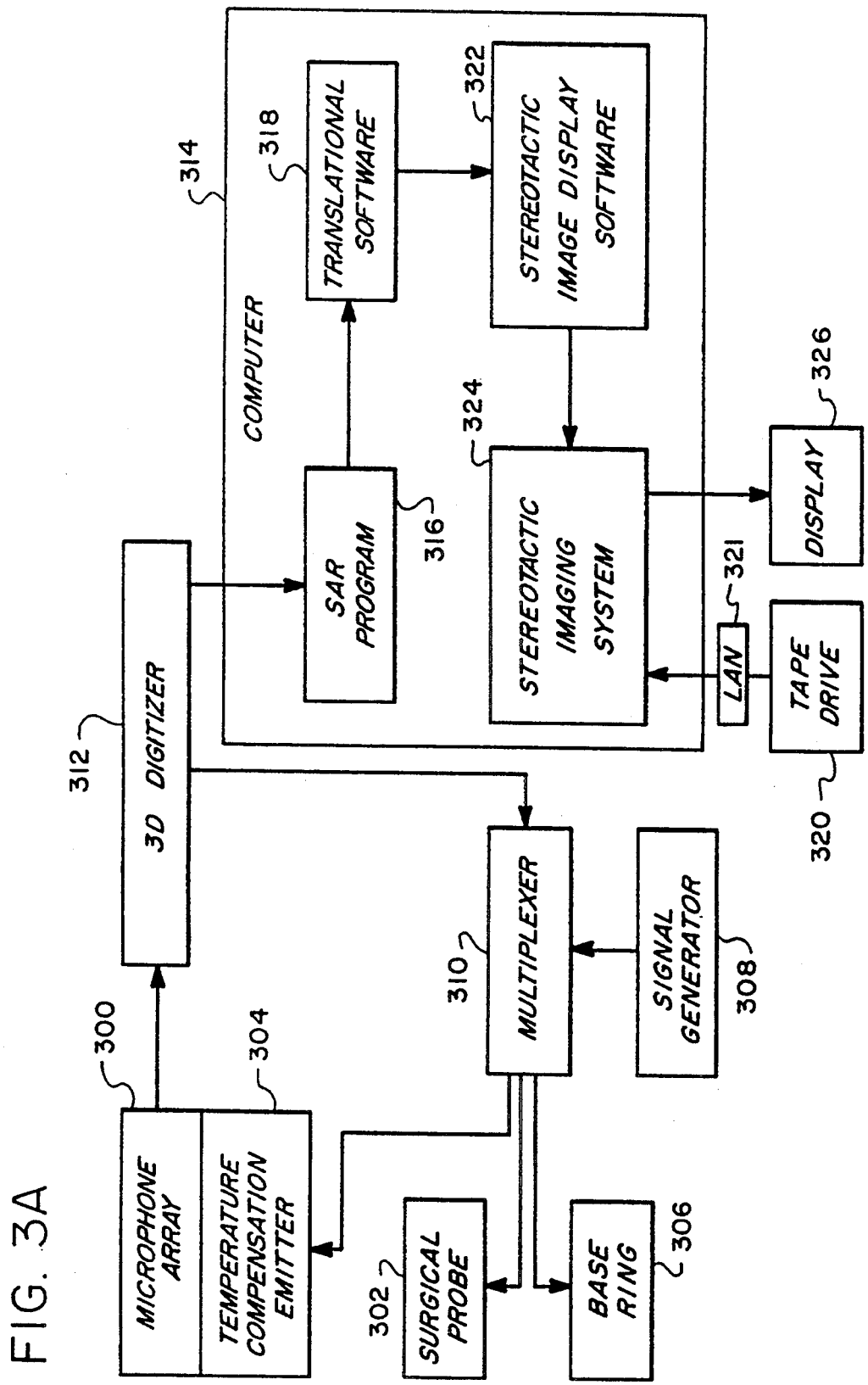
FIG. 3A is a block diagram of a system according to the invention for indicating the position of a surgical probe within a head on an image of the head.
Figure 3B:
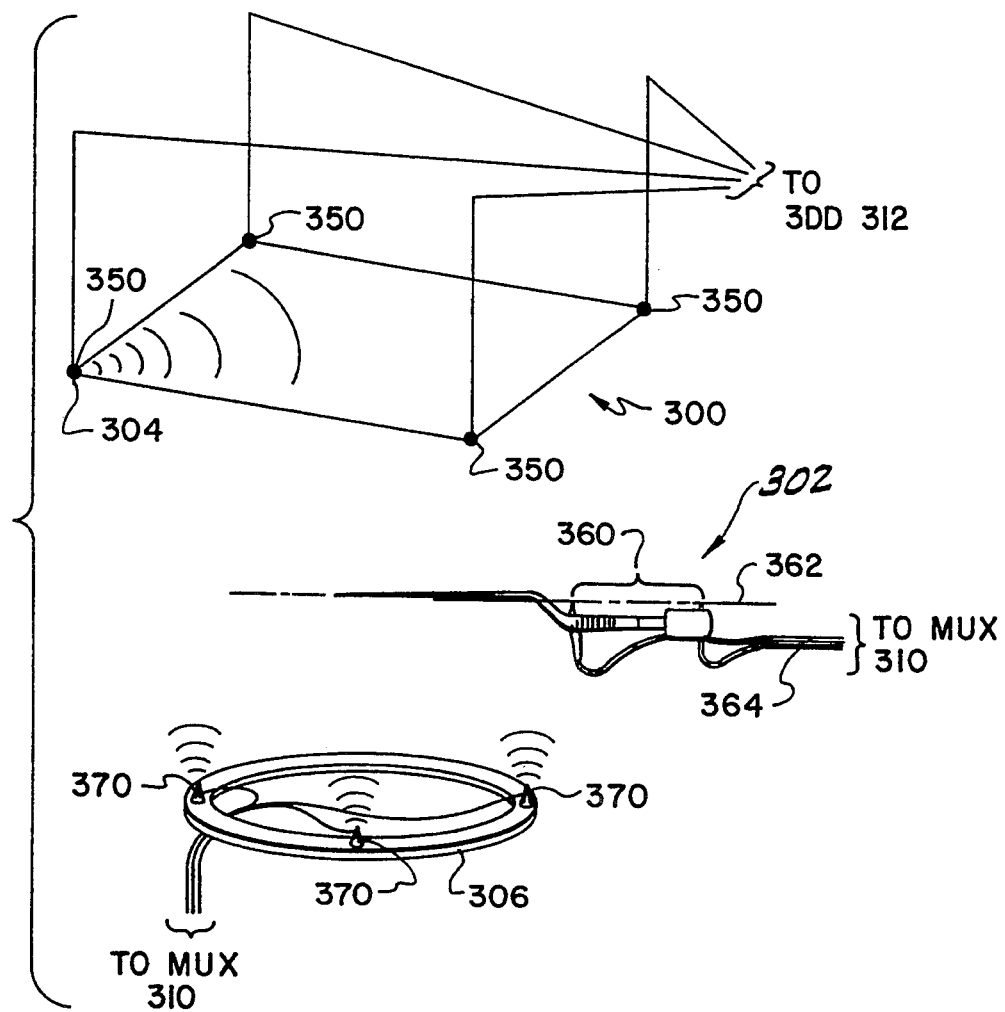
FIG. 3B is a perspective schematic diagram of the microphone array, surgical probe and base ring according to the invention.

In particular, an off-the-shelf, three dimensional sonic digitizer such as Model GP-8-3D produced by Scientific Accessories Corporation is used to determine the position of the probe. As shown in FIG. 3A, the 3D digitizer system includes a microphone array 300 which is generally mounted in the operating room on the ceiling or in some other position so that it is in a line of sight with the surgical probe 302 that is being used. As will be described in greater detail below, the probe 302 includes transmitters such as sound emitters thereon which interact with the microphone array 300 so that the position of the tip of surgical probe 302 is known at any particular instant in time. The 3D digitizer system also includes a temperature compensation emitter 304 associated with the microphone array 300. Furthermore, mounted to the ring 120 (FIG. 1C) affixed to the patient's head is a base ring 306 which is coaxial and parallel with the plane defined by reference ring 120. This base ring 306 includes a plurality of transmitters as will be described below which interact with the microphone array 300 so that the relative position of the base ring 306 can be determined any particular instant in time. Signal generator 308 generates a signal which is provided through a multiplexer 310 to the temperature compensation emitter 304, surgical probe 302, and base ring 306. Usually, temperature compensation emitter 304 is activated by the signal generator 308 via multiplexer 310 to emit a signal which is received by the microphone array 300. Each of the signals received by each of the microphones of the array 300 is provided to a digitizer 312 which digitizes the signals and provides the digitized signals to computer 314 which includes a spatial acquisition and recording (SAR) program 316 which acquires and records spatial coordinates based on the digitized signals. For example, program 316 may be the SACDAC program licensed by PIXSYS of Boulder, Colo. This program evaluates the digitized signals emitted by the temperature compensation emitter 304 to determine the reference standards. i.e., the velocity of the radiation through the air. For example, depending on the temperature of the air in the operating room, the period of time that it takes from the instant that the temperature compensation emitter 304 is actuated to radiate a signal until the instant that each of the microphones of the array 300 receives the emitted signal will vary. The SAR program 316 knows, through calibration, the distance between the temperature compensation emitter 304 and each of the microphones of the array 300. Therefore, the SAR program 316 can immediately calculate the velocity of the signals being transmitted. This velocity establishes a reference for determining the position of the surgical probe 302 and the base ring 306.

Next, the emitters of the base ring 306 are activated so that the position of the base ring 306 can be determined. At this point, the emitters of the base ring 306 are successively energized and the radiation transmitted by these emitters is detected by the microphone array 300. The signal generated by the microphones from this radiation is digitized and evaluated by the SAR program 316 to determine the position of each of the emitters of the base ring 306. Once the positions of the base ring emitters have been determined by the SAR program 316, standard geometrical computations are performed by the SAR program to determine the plane defined by the base ring 306 with respect to the microphone array 300.

Digitizer 312 then signals multiplexer 310 to provide the signal generated by signal generator 308 to the surgical probe 302. At this point, the emitters of the surgical probe 302 are successively energized and the radiation transmitted by these emitters is detected by the microphone array 300. The signal generated by the microphones from this radiation is digitized and evaluated by the SAR program 316 to determine the position of each of the emitters of the surgical probe 302. Once the positions of the probe emitters have been determined by the SAR program 316, standard geometrical triangulation is performed by the SAR program to determine the location of the tip of the surgical probe with respect to the microphone array 300.

Therefore, by using the 3D digitizer system, the position of the base ring 306 and the position of the surgical probe 302 relative to the base ring 306 can be determined by the SAR program 316. As noted above, the base ring 306 is mounted to the reference ring 120 (FIG. 1C) and is essentially coplanar therewith so that the base ring 306 defines the reference plane RP of the scanned image coordinate system illustrated in FIG. 1D.

Computer 314 includes translational software 318 which then translates the coordinates of surgical probe coordinate system illustrated in FIG. 2D into the scanned image coordinate system illustrated in FIG. 1D. As a result of this translation, computer 314 has now determined the particular scanned image of the preoperative scan on which the tip of the surgical probe 302 would be located. The system includes a tape drive 320, accessed through a local area network (LAN) 321, in which each of the images of the preoperative scan are stored. The translated coordinates generated by translational software 318 are provided to the stereotactic image display software 322, also resident within computer 314, and identify the particular scanned image which is to be viewed by the surgeon. The identified image is selected by the stereotactic imaging system 324 which recreates the image from the data stored in tape drive 320 and displays it on a high resolution display 326. Stereotactic image display software 322 and stereotactic image system 324 may be any off-the-shelf system such as manufactured by Stereotactic Image Systems, Inc. of Salt Lake City, Utah.

Referring to 3B, a perspective illustration of the microphone array 300, temperature compensation emitter 304, surgical probe 302 and base ring 306 are illustrated. Microphone array 300 includes a plurality of microphones 350, the outputs of which are connected to 3D digitizer 312. Adjacent to the microphone array 300 is a temperature compensating emitter 304 which selectively emits signals used by the SAR program in calibration to determine the velocity of the radiation. For example, in the Scientific Accessories Corporation Model GP-8-3D, a sonic digitizer is used. In this case, the speed of sound being transmitted from the temperature compensation emitter 304 to the microphones 350 is calculated by the SAR program to determine the speed at which the sound is being transmitted through the air. Since this system is very accurate and the speed of sound varies fairly significantly with respect to the temperature of the air, the temperature compensation emitter 304 allows the 3D digitizer system to compensate for changes in the air temperature in the operating room. Surgical probe 302 comprises a bayonet surgical forceps modified to carry at least two sound emitters 360 thereon which are essentially coaxial on axis 362 with the tip of the forceps. The emitters are in line and immediately below the surgeon's line of sight through the forceps so that the line of sight is not blocked. In general, the microphone array 350 is attached to the operating light above the patient's head so that it is in direct line of sight with the forceps as they are being used by the surgeon. The microphones 350 listen to the sound emitted from the sequential energization of the emitters 360 on the forceps. The SAR software 316 measures the time of transmission from each of the sound emitters 360 on the forceps to the microphones 350. By comparing these times, the position of both emitters 360 and, therefore, the tip of the forceps can be calculated by the SAR program 316.

Base ring 306 is affixed to the reference ring 20 attached to the patient's head and is essentially coplanar with the reference points RP1, RP2 and RP3. Base ring 306 includes a plurality of emitters 370 thereon which are connected to multiplexer 310 and energized by signal generator 308. Each one of these emitters 370 is sequentially energized so that the radiation emitter thereby is received by the microphones 350 of array 300. The emitters 370 are preferably positioned 90° apart with the center emitter being located at the anterior of the head. This permits base ring 306 to be mounted around the head so that all three emitters are in line of sight with the array. The resulting signals are digitized by digitizer 312 so that the SAR program 316 is able to determine the plane in which the emitters 370 are located. This plane essentially defines the reference plane because it is coplanar with the reference points RP1, RP2 and RP3. By determining the position of the reference plane, translational software 318 is now able to take the coordinate position of the probe 302 and translate it from the surgical probe coordinate system of FIG. 2D into the scanned image coordinate system as illustrated in FIG. 1D. As a result, the particular scanned image which corresponds to the position of the probe can be identified and displayed for viewing by the surgeon.

The surgical probe 302 is generally a bayonet cauterizing device which has a bundle of wire 364 attached thereto. Therefore, the wires required to connect the emitters 360 to the multiplexer 310 are part of the bundle of wires 364 which connect the forceps to its electrical power source and the surgeon is familiar with handling such forceps connected to a wire bundle. Therefore, there is no inconvenience to the surgeon in using such a probe and the surgeon is familiar with handling such a forceps connected to a wire bundle.

Base ring 306 is one apparatus for determining and positioning the reference points RP1, RP2 and RP3 with respect to the microphone array 300. An advantage of the base ring 306 is that each time the patient's head is moved the base ring 306 is energized to define the reference plane. This allows the surgeon to move the patient's head during surgery. Alternatively, the reference points RP1, RP2 and RP3 can be established by using a reference mode of the 3D digitizer 312. In particular, the tip of probe 302 is positioned on each of the reference points RP1, RP2 and RP3 and actuated to emit a signal to the microphone array 300 so that the position of the tip can be determined at each of these points. This is performed during a reference mode of operation of the 3D digitizer 312 so that the SAR program 316 calculates, at the end of the execution of this mode, the position of the reference points RP1, RP2 and RP3. This requires that the reference points have to be reestablished before the position of the surgical probe is determined to avoid changes in the reference plane due to movement of the head. On the other hand, one advantage of this approach is that the use of the reference ring 120 may be eliminated. In particular, it is possible that the reference pins 124 can be permanently affixed to the skull of the patient. For example, these pins may be radiolucent surgical screws which are embedded in the patient's skull and which have radiopaque tips. These screws would be affixed to the patient's skull before surgery and before the preoperative scanning so the radiopaque tips would provide a constant reference during scanning and throughout the stereotactic surgical procedure. During the actual surgery, the probe would be used to indicate the position of each of the radiopaque tips before the probe position was determined. By eliminating the need for the reference ring 124, other advantages are also achieved. For example, generally the preoperative scanning must be done under anesthetic because the reference ring 120 interferes with intubation. Therefore, intubation must occur before the reference ring is affixed to the skull. By eliminating the need for the reference ring 120 and using surgical screws to identify the reference points RP1, RP2 and RP3, the preoperative scanning can be performed without the need for intubation and the anesthesia accompanying it. In one alternative embodiment, it is contemplated that the emitters 370 may each be separately mounted to a screw or other fixed structure positioned at one of the reference points.

Figure 3C:
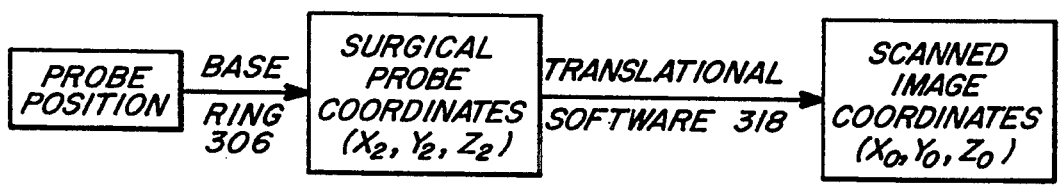
FIG. 3C is a block diagram of the steps involved in the process according to the invention for determining the position of a surgical probe relative to the scanned images so that the image corresponding to the probe position can be identified and viewed by the surgeon.

In summary, this process according to the invention is illustrated in FIG. 3C and identifies the location of the tip of the surgical probe 202 for the surgeon. Initially, the reference plane is determined by energizing the base ring 306 or by positioning the probe 302 at the reference points (as described herein). Next, the surgeon positions the probe in the position desired within the head. The emitters of the probe are then energized so that the probe position is measured and determined in the surgical probe coordinate system $(X_2, Y_2, Z_2)$. Next, the translational software 318 converts the surgical probe coordinate system into the scanned image coordinate system $(X_0, Y_0, Z_0)$ so that the image corresponding to the probe position can be displayed.

Referring to FIG. 4, a flow chart of the operation of the translational software 318 is illustrated. Initially, the surgeon locates the probe 302 in the position which is to be determined. (If a base ring 306 is not being used to identify the location of the reference plane, the initial step is for the surgeon to use the reference mode of the 3D digitizer 312 to identify the reference plane by locating the surgical probe tip at several points in the plane.)

The system initializes at step 400 so that translational software opens a window menu at step 402 of a multitasking program such as DESQ VIEW distributed by Quarterdeck Office Systems of Santa Monica, Calif. Such software permits simultaneous execution of multiple software programs. In general, once a program is selected for actuation, it continues to run either in the foreground or in the background until deactuated.

The translational software continues initializing by selecting the stereotactic imaging system and actuating the stereotactic imaging system in the foreground by opening the stereotactic window at step 404. Thereafter, the translational software returns to the window menu at step 406 moving the stereotactic image display software to the background and selects the digitizer window at step 408 to actuate the digitizer in the foreground. The computer is then ready to be actuated by the foot switch.

The surgeon then actuates a foot pedal or other switch which indicates that the system should perform a computation. Actuation of the foot switch is essentially the beginning of the start step 410. Upon actuation, the digitizer energizes calibration by the temperature compensation emitter 304 to determine the velocity of the sound waves, energizes the emitters of the base ring 306 to locate the reference plane and energizes the emitters of the surgical probe 302 to locate the position of the tip of the probe 302. The signals generated by the microphone array are digitized so that the SAR program 316 determines the coordinates of the tip of the surgical probe. At step 412, the translational software 318 selects the coordinates from the SAR program.

Next, the window menu is again accessed at step 414 and the window menu switches to the stereotactic image system software to the foreground at step 416 to specifically control the operation of the stereotactic imaging system 324. At this point, the translational software 318 issues an F1 command to the stereotactic image display software 322 which in turn prepares the stereotactic imaging system 324 to accept coordinates. At step 420, the window menu is again selected so that at step 422 the completer switches the digitizer window into the foreground. At step 424, the digitizer window menu is accessed and coordinate translation is selected. At step 426, the digitizer begins calculating the coordinates and at step 428 the coordinate calculation is ended. The translational software then returns to the digitizer window menu at step 430, switches windows to place the stereotactic image system software in the foreground at 432 to prepare it for receiving the coordinates and again returns to the main window menu at step 434. Finally, the coordinate information is translated, including any necessary manipulation, and transferred to the stereotactic image display software 322 at step 436 which actuates the stereotactic imaging system 324 to select the particular image from the tape drive 320 and display it on high resolution display 326. The stereotactic image display software 322 instructs the stereotactic imaging system 324 to display the image closest to transferred coordinates and to display a cursor on the display 326 at the coordinates which corresponds to the position of the tip of the probe. Thereafter, the computer 314 is in a standby mode until the foot switch of the surgeon is again actuated to execute the translational software beginning with the start step 410.

The translation that occurs in step 436 depends on the position of the surgical probe coordinate system relative to the scanned image coordinate system and the units of measure. In the preferred embodiment, the systems are coaxial and the units of measure are the same so that algebraic adjustment is unnecessary. However, it is contemplated that the coordinates systems may not be coaxial, in which case translation would require arithmetic and/or trigonometric calculations. Also, the sequence, e.g., $(X_2, Y_2, Z_2)$, in which the coordinates are generated by the digitizer may be different than the sequence, e.g., $(X_0, Y_0, Z_0)$, in which stereotactic image system software receives coordinates. Therefore, the sequence in which the coordinates are transferred may have to be reordered.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A system for indicating a location within a body of a patient, said system comprising:

reference points means having a position in fixed relation to the body for providing reference points;

means for generating images of the body, said images including reference images corresponding to the reference points means;

reference means having a location outside the body for providing a reference;

a surgical probe including a tip having a position;

first means for determining the position of the tip of the surgical probe relative to the reference means;

second means for determining the position of the reference points means of the body relative to the reference means so that the position of the tip relative to the reference points means of the body is a known position;

means for translating the known position of the tip of the surgical probe to provide a translated position within a coordinate system corresponding to the images of the body; and means for displaying an image of the body to provide a displayed image which corresponds to the translated position of the tip of the surgical probe.

2. The system of claim 1 wherein the displaying means comprises:

means for displaying an image representing the tip of the probe on the displayed image of the body.

3. The system of claim 2 wherein the second means comprises:

a base adapted to be mounted on the body in a position having a fixed relationship with the reference points means of the body; and means for measuring the position of the base with respect to the reference means.

4. The system of claim 3 wherein the reference means comprises an array having sensors and wherein the probe comprises a bayonet forceps having emitters in line worth the tip of the forceps and below a surgeon's line of sight when using the forceps, said emitters for communicating with the sensors of the array to indicate a position of the probe relative to the array.

5. The system of claim 4 further comprising additional emitters on the base for communicating with the sensors of the array to indicate the position of the base relative to the array.

6. The system of claim 4 further comprising three dimensional digitizer means for digitizing signals generated the sensors in response to signals from the emitters.

7. The system of claim 1 wherein the translating means comprises a computer connected between the second means and the displaying means and a translational software program for controlling the operation of the computer so that coordinates supplied to the computer by the second means are converted into corresponding coordinates supplied to the displaying means.

8. The system of claim 1 wherein the displaying means comprises an imaging system.

9. The system of claim 1 further comprising means for compensating for temperature changes which affect the operation of the first and second determining means.

10. The system of claim 1 wherein the displaying means comprises means for displaying a cursor representing the tip of the probe on the displayed image of the body.

11. The system of claim 1 wherein the reference points define a reference plane and wherein the coordinate system of the images includes an X-Y plane parallel to the reference plane.

12. The system of claim 1 wherein the reference means comprises an array having sensors and wherein the probe comprises a bayonet forceps having a line of sight through the forceps and having two emitters mounted on the forceps which are in line with the tip of the forceps and below the line of sight through the forceps, said emitters for communicating with the sensors of the array to indicate the position of the probe relative to the array.

13. The system of claim 1 further comprising radiolucent pins having radiopaque tips, said pins adapted to be located on the body so that said tips define the reference points means.

14. A method for indicating a position of a tip of a surgical probe which is positioned within a body of a patient on images of the body wherein the body and the images of the body include reference images corresponding to reference points in a position on the body, said method comprising the steps of:

determining the position of the tip of the surgical probe relative to a reference means having a location outside the body;

determining the position of the reference points of the body relative to the reference means so that the position of the tip relative to the reference points of the body is a known position;

translating the known position of the tip of the surgical probe to provide a translated position within a coordinate system corresponding to the images of the body; and displaying an image of the body which corresponds to the translated position of the tip of the surgical probe.

15. The method of claim 14 wherein the displaying step comprises the step of:

displaying an image representing the tip of the surgical probe on the corresponding image of the body.

16. The method of claim 14 wherein the reference means comprises an array having sensors and wherein the step of determining the position of the reference points of the body relative to the reference means comprises the steps of mounting a base on the body in a position having a fixed spatial relationship with the reference points of the body and measuring the position of the base with respect to the array.

17. The method of claim 16 further comprising the step of emitting radiation from the base to the array to indicate the position of the base.

18. The method of claim 14 wherein the step of determining the position of the reference points of the body with respect to the reference means comprises the steps of placing the tip of the probe at the reference points and determining the position of the tip at the reference points to define the position of the reference points with respect to the reference means.

19. The method of claim 14 further comprising the step of compensating for temperature changes affecting the first and second determining steps.

20. A system for indicating a position within an object, said system comprising:

reference points means having a position in fixed relation to the object for providing reference points;

means for generating images of the object, said images including reference images corresponding to the reference points means;

reference means having a location outside the object for providing a reference;

a probe including a tip having a position;

first means for determining the position of the tip of the probe relative to the reference means;

second means for measuring the position of the reference points means of the object relative to the reference means so that the position of the tip relative reference points means of the object is a known position;

means for translating the known position of the tip of the probe to provide a translated position within a coordinate system corresponding to the images of the object; and means for displaying an image of the object which corresponds to the translated position of the tip of the probe.

* * * * *

UNITED STATES PATENT AND TRADEMARK OFFICE
CERTIFICATE OF CORRECTION

REEXAMINATION
PATENT NO. : B1 5,383,454
DATED      : December 31, 1996
INVENTOR(S): Richard D. Bucholz It is certified that error appears in the above-identified patent and that said Letters Patent is hereby corrected as shown below:

On the title page,
[73]Assignee, is corrected to read:

"St. Louis University, St. Louis, Mo."

Signed and Sealed this

Fifteenth Day of June, 1999

Attest:

Q. TODD DICKINSON

Attesting Officer                Acting Commissioner of Patents and Trademarks

REEXAMINATION CERTIFICATE (3091st)

United States Patent [19]

Bucholz

[11] B1 5,383,454

[45] Certificate Issued Dec. 31, 1996

[54] SYSTEM FOR INDICATING THE POSITION OF A SURGICAL PROBE WITHIN A HEAD ON AN IMAGE OF THE HEAD

[75] Inventor: Richard D. Bucholz, St. Louis, Mo.

[73] Assignee: Sofamor Danek Group, Inc., Memphis, Tenn.

Reexamination Request:
No. 90/003,899, Jul. 24, 1995

Reexamination Certificate for:
Patent No.: 5,383,454
Issued: Jan. 24, 1995
Appl. No.: 909,097
Filed: Jul. 2, 1992

Related U.S. Application Data

[63] Continuation of Ser. No. 600,753, Oct. 19, 1990, abandoned.

[51] Int. Cl.$^6$ .................................................. A61B 5/103
[52] U.S. Cl. ...................................... 128/653.1; 606/130

[56] References Cited

U.S. PATENT DOCUMENTS

| | | | |
|---|---|---|---|
| 4,058,114 | 11/1977 | Soldner . | |
| 4,068,156 | 1/1978 | Johnson et al. | 318/575 |
| 4,068,556 | 1/1978 | Foley | 89/1.814 |
| 4,358,856 | 11/1982 | Stivender et al. | 378/167 |
| 4,407,298 | 10/1983 | Lentz et al. | 128/713 |
| 4,457,311 | 7/1984 | Sorenson et al. . | |
| 4,465,069 | 8/1984 | Barbler et al. . | |
| 4,473,074 | 9/1984 | Vassiliadis . | |
| 4,506,676 | 3/1985 | Duska | 128/653 |
| 4,571,834 | 2/1986 | Fraser et al. | 33/1 PT |
| 4,583,538 | 4/1986 | Onik et al. . | |
| 4,592,352 | 6/1986 | Patil . | |
| 4,602,622 | 7/1986 | Bar et al. . | |
| 4,645,343 | 2/1987 | Stockdale et al. | 356/326 |
| 4,659,971 | 4/1987 | Suzuki et al. | 318/568 |
| 4,674,057 | 6/1987 | Caughman et al. | 364/513 |
| 4,686,997 | 8/1987 | Oloff et al. . | |

(List continued on next page.)

FOREIGN PATENT DOCUMENTS

| | | |
|---|---|---|
| 0018166 | 4/1980 | European Pat. Off. . |
| 0326768 | 12/1988 | European Pat. Off. . |
| 0359773 | 3/1990 | European Pat. Off. . |
| 0427358 | 10/1990 | European Pat. Off. . |
| 0456103 | 5/1991 | European Pat. Off. . |
| 79 2417970 | 2/1979 | France . |
| 2534516 | 10/1975 | Germany . |
| 2852949 | 12/1978 | Germany . |
| 3205915 | 9/1983 | Germany . |
| 8701668.0 | 2/1987 | Germany . |
| 2094590 | 2/1982 | United Kingdom . |

OTHER PUBLICATIONS

Mesqui, et al., "Real–Time, Noninvasive Recording and Three–Dimensional Display of the Functional Movements of an Arbitrary Mandible Point," 1985, Biostereometrics, vol. 602 pp. 77–83.

Brown, "A Stereotactic Head Frame for Use with CT Body Scanners," 1979, Investigative Radiology, vol. 14, No. 4, pp. 300–304.

Reinhardt et al., "Interactive Sonar–Operated Device for Stereotactic and Open Surgery," Stereotac Funct Neurosurg 1990; 54+55:393–397.

(List continued on next page.)

*Primary Examiner*—Ruth S. Smith

[57] ABSTRACT

A system for indicating a position of a tip of a probe which is positioned within an object on cross-sectional, scanned images of the object. The object includes reference points and the images of the object include reference images corresponding to the reference points. An array for receiving radiation emitted from the probe and from time reference points is digitized by a three dimensional digitizer to measure the position of the tip of the probe relative to the reference points of the object:. A computer employing translational software translates the position of the tip of the probe into a coordinate system corresponding to the coordinate system of the cross-sectional images. A stereotactic imaging system selects the image of the object closest to the measured position of the tip of the probe and displays the selected image and a cursor representing the position of the tip of the probe on the selected images.

U.S. PATENT DOCUMENTS

| | | | |
|---|---|---|---|
| 4,698,777 | 10/1987 | Toyoda et al. | 364/513 |
| 4,701,407 | 10/1987 | Seppel | 435/1 |
| 4,722,056 | 1/1988 | Roberts et al. | 364/413 |
| 4,733,661 | 3/1988 | Palestrant . | |
| 4,742,815 | 5/1988 | Ninan et al. . | |
| 4,753,128 | 6/1988 | Bartlett et al. | 74/469 |
| 4,762,016 | 8/1988 | Stoughton et al. | 74/479 |
| 4,776,749 | 10/1988 | Wanzenberg et al. | 414/680 |
| 4,821,206 | 4/1989 | Arora | 364/513 |
| 4,835,710 | 5/1989 | Schnelle et al. | 364/513 |
| 4,933,843 | 6/1990 | Scheller et al. | 364/413.01 |
| 4,943,296 | 7/1990 | Funakubo et al. | 606/166 |
| 4,954,043 | 9/1990 | Yoshida et al. | 414/719 |
| 4,955,891 | 9/1990 | Carol | 606/130 |
| 4,961,422 | 10/1990 | Marchosky et al. . | |
| 5,047,036 | 9/1991 | Koutrouvelis | 606/130 |
| 5,050,608 | 9/1991 | Watanabe et al. . | |
| 5,078,140 | 1/1992 | Kwoh | 128/653.1 |
| 5,080,662 | 1/1992 | Paul | 606/130 |
| 5,086,401 | 2/1992 | Glassman et al. | 395/94 |
| 5,186,174 | 2/1993 | Schlondorff et al. | 128/653.1 |
| 5,193,106 | 3/1993 | DeSena | 378/163 |
| 5,207,223 | 5/1993 | Adler | 128/653.1 |
| 5,230,338 | 7/1993 | Allen et al. | 128/653 |
| 5,251,127 | 10/1993 | Raab | 364/413.13 |
| 5,305,203 | 4/1994 | Raab | 364/413.13 |

OTHER PUBLICATIONS

Watanabe, "Neuronavigator," Igaku-no-Ayumi, vol. 137, No. 6 May 10, 1986 (With Translation).

Mazier, et al., "Computer Assisted Interventionist Imaging: Application to the Vertebral Column Surgery," IEEE, vol. 12, No. 1, 1990.

Lavallee, "A New System for Computer Assisted Neurosurgery," IEEE, 1989.

Reinhardt et al., "CT-Guided 'Real Time' Stereotaxy," Acta Neurochirurgica Suppl. 46, 107-108, 1989.

Reinhardt, "Surgery of Brain Neoplasms Using 32-P Tumour Marker," Acta Neurochir 97; 89-94, 1989.

Jacques, et al., "A Computerized Microstereotactic Method to Approach, 3-Dimensionally Reconstruct, Remove and Adjuvantly Treat Small CNS Lesions," Appl. Neurophysiol. 43: 176-182, 1980.

Adams, et al., "Computer-Assisted Surgery," Medical Imaging, IEEE, pp. 43-51, May 1990.

Cinquin et al., "Computer Assisted Medical Interventions," IARP, pp. 63-65, Sep. 1989.

Mazier et al., "Chirurgie De La Colonne Vertebrale Assistee Par Ordinateur: Application Au Vissage Pediculaire," Innov. Tech. Biol. Med.; vol. 11, n°5, pp. 559-566, 1990.

Lavallee et al., "Computer Assisted Driving of a Needle into the Brain," CAR, pp. 416-420, 1989.

Lavallee, et al., "Computer Assisted Interventionist Imaging: The Instance of Stereotactic Brain Surgery," MED-INFO, 1989.

Lavallee, et al., "Computer Assisted Puncture," Afcet, pp. 439-449, Nov. 1987.

Lavallee et al., "Computer Assisted Medical Interventions," NATO ASI Series, vol. F60, pp. 302-312, 1990.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–20 is confirmed.

* * * * *